United States Patent

Gründler et al.

[11] Patent Number: 5,817,838
[45] Date of Patent: Oct. 6, 1998

[54] PROCESS FOR MANUFACTURING CYCLOCARBONATES USING A SILVER SALT CATALYST

[75] Inventors: Hansjörg Gründler, Rheinfelden; Hans-Jürgen Hansen, Zurich, both of Switzerland

[73] Assignee: Roche Vitamins Inc., Parsippany, N.J.

[21] Appl. No.: 946,844

[22] Filed: Oct. 8, 1997

[30] Foreign Application Priority Data

Oct. 21, 1996 [EP] European Pat. Off. ............. 96116895

[51] Int. Cl.$^6$ ...................... C07D 317/12; C07D 317/14
[52] U.S. Cl. ............................................ 549/230; 549/229
[58] Field of Search ..................... 549/229, 230

[56] References Cited

FOREIGN PATENT DOCUMENTS 0 175 241   7/1995   European Pat. Off. .
1098953   8/1961   Germany .

OTHER PUBLICATIONS

Yanagihara et al., 52nd National Meeting of the Chemical Society of Japan, Kyoto, Abstract No. 4W 15 (1986).
Sasaki, *Tetrahedron Letters*, 27(14):1573–1574 (1986).
Inoue et al., *The Chemical Society of Japan*, 60(3):1204–1206 (1987).
Fournier et al., *Tetrahedron Letters*, 30(30):3981–3982 (1989).
Joumier et al., *J. Chem. Soc. Perkin Trans 1*, 3271–3274 (1991).
Marshall et al., *J. Org. Chem.*, 60:5966–5968 (1995).
Ogawa et al., *Synlett*, 871–872 (1995).
Ogawa et al., *Heterocycles* 41(11):2587–2599 (1995).
Laas et al., *Synthesis*, 958–959 (1981).

*Primary Examiner*—Johann Richter
*Assistant Examiner*—Dominic Keating
*Attorney, Agent, or Firm*—George W. Johnston; William H. Epstein; John P. Parise

[57] ABSTRACT

A process for the manufacture of 4,4-disubstituted 5-methylene-1,3-dioxolan-2-ones ("cyclocarbonates") of the formula:

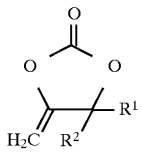

wherein $R^1$ and $R^2$ each independently signify a saturated or olefinically-unsaturated aliphatic group or an aromatic group, or $R^1$ and $R^2$ together form tetra- or pentamethylene, by reacting a corresponding 3,3-disubstituted prop-1-yn-3-ol of the formula $HC\equiv C-C(R^1)(R^2)-OH$ (II) with carbon dioxide in the presence of a quaternary ammonium or phosphonium salt as the catalyst comprises using a silver salt as a further catalyst. An alkali metal or quaternary ammonium or phosphonium salt of a carboxylic acid can also be used to increase the catalytic performance of the silver salt catalyst. Moreover, the addition of triphenylphosphine serves to accelerate the reaction to some extent. The silver salts catalyze this process significantly better than the previously utilized copper salts. Advantageously, the process uses much smaller amounts of catalyst, significantly shortens reaction times, and mandates less drastic reaction conditions. Cyclocarbonates produced by this process are valuable intermediates for the production of polymerizates and other useful substances, such as dyestuffs and carotenoids.

25 Claims, No Drawings

PROCESS FOR MANUFACTURING CYCLOCARBONATES USING A SILVER SALT CATALYST

BACKGROUND OF THE INVENTION

1. Field

The present invention is concerned with an improved process for the manufacture of cyclic carbonates (cyclocarbonates) from prop-1-yn-3-ols and carbon dioxide in the presence of catalysts. These cyclocarbonates, of which the structurally simplest member is 4,4-dimethyl-5-methylene-1,3-dioxolan-2-one (also known itself as "cyclocarbonate"), are valuable intermediates for the production of polymerizates and other useful substances, such as dyestuffs and carotenoids.

2. Description

Known processes for manufacturing cyclocarbonates, such as 4,4-disubstituted 5-methylene-1,3-dioxolan-2-ones of the formula:

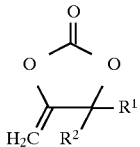

(defined in more detail later), involve catalyzed reaction of the corresponding 3,3-disubstituted prop-1-yn-3-ol of the formula:

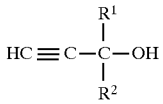

with carbon dioxide. Copper salts, especially copper halides, such as copper(II) chloride and copper(I) iodide, and copper (II) acetate [see German Patent 1,098,953, Synthesis 1981, 958–959 and European Patent Publication (EP) 175 241], diacetonitrilopalladium dichloride (N. Yanagihara et al., 52$^{nd}$ National Meeting of the Chemical Society of Japan, Kyoto April 1986, Abstr. No. 4W 15), ruthenium trichloride trihydrate together with triethylamine [Tetr. Lett. 27 (14):1573–1574 (1986)], dicyclopentadienylcobalt, also together with triethylamine [Bull. Chem. Soc. Japan 60: 1204–1206 (1987)], as well as tributylphosphine [Tetr. Lett. 30 (30): 3981–3982 (1989)] have been used as catalysts. It has not previously been known that silver salts also catalyze this reaction.

It has now been found that the above reaction, which leads to the 4,4-disubstituted 5-methylene-1,3-dioxolan-2-ones of formula I, can also be catalyzed by silver salts, with a quaternary ammonium or phosphonium salt being used as a further catalyst—as proposed in EP 175 241. In contrast to the teaching of EP 175 241 a tertiary base is not used as an additional catalyst for this process, or its use is superfluous. The present invention differs from that of EP 175 241 in that a silver salt is used as the catalyst instead of a copper salt.

SUMMARY OF THE INVENTION

The subject invention provides a process for manufacturing 4,4-disubstituted 5-methylene-1,3-dioxolan-2-ones of the formula:

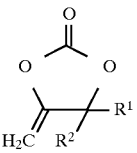

wherein $R^1$ and $R^2$ each independently is a saturated aliphatic group, an olefinically-unsaturated aliphatic group or an aromatic group, or $R^1$ and $R^2$ together form tetramethylene or pentamethylene. This process comprises reacting a corresponding 3,3-disubstituted prop-1-yn-3-ol of the formula:

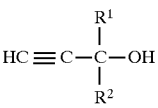

with carbon dioxide in the presence of a first catalyst selected from the group consisting of quaternary ammonium salts and phosphonium salts, and a second catalyst which is a silver salt.

DETAILED DESCRIPTION OF THE INVENTION

The present invention will now be described in terms of its preferred embodiments. These embodiments are set forth to aid in understanding the invention, but are not to be construed as limiting.

The present invention is a process for manufacturing 4,4-disubstituted 5-methylene-1,3-dioxolan-2-ones of the formula:

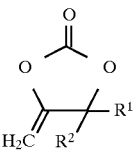

wherein $R^1$ and $R^2$ each independently signify a saturated or olefinically-unsaturated aliphatic group or an aromatic group, or $R^1$ and $R^2$ together form tetra- or pentamethylene, by reacting a corresponding 3,3-disubstituted-prop-1-yn-3-ol of the formula:

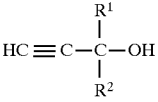

with carbon dioxide in the presence of a quaternary ammonium or phosphonium salt as the catalyst, which process comprises using a silver salt as a further catalyst.

In the above definition of the process in accordance with the invention the term "a saturated aliphatic group" includes alkyl groups with from about 1 to about 16 carbon atoms, which can be straight-chain or (from $C_3$) branched. Also, the "olefinically-unsaturated aliphatic group" (an alkenyl group) contains especially up to about 16 carbon atoms (preferably from 2 to 16 carbon atoms) and can be straight-chain or branched. Moreover, this group can be mono- or multiply unsaturated, and several double bonds can be conjugated or non-conjugated. Examples of these alkyl and alkenyl groups are methyl, ethyl, isopropyl, isobutyl, tert.butyl and 4,8-dimethyl-nonyl and, respectively, vinyl, 1-propenyl, allyl, 4-methyl-3-pentenyl, 4,8-dimethyl-1,7-nonadienyl, and 4,8- dimethyl-1,3,7-nonatrienyl. As the "aromatic group" there comes into consideration especially phenyl or naphthyl, each of which is optionally substituted, for example with one or more (same or different) $C_{1-4}$-alkyl and $C_{2-4}$-alkenyl groups and halogen atoms. Phenyl, p-toluyl and naphthyl are examples of the aromatic groups.

When $R^1$ and $R^2$ together signify tetra- or pentamethylene, then a cyclopentane or cyclohexane ring is present together with the carbon atom to which $R^1$ and $R^2$ are attached.

In principle, all silver salts such as silver acetate, silver sulphate, silver orthophosphate, silver oxide and silver carbonate are suitable for use accordance with the invention. Silver acetate or silver sulphate is preferably used as the silver salt catalyst.

A quaternary ammonium or phosphonium salt is also used as a catalyst in the process in accordance with the invention. This salt conveniently has the formula:

$(R^3)_4N^+$ $Hal^-$            IIIa or $(R^3)_4P^+$ $Hal^-$            IIIb wherein each $R^3$ independently signifies $C_{1-6}$-alkyl, $C_{5-7}$-cycloalkyl, aryl-$C_{1-4}$-alkyl or aryl and Hal signifies halogen.

In this definition any alkyl group or any alkylene part of the aryl-$C_{1-4}$-alkyl group can be straight-chain or branched. Under the term "aryl" (as such or as part of the aryl-$C_{1-4}$-alkyl group) there are to be understood especially phenyl and naphthyl, with such a group being unsubstituted or substituted, conveniently with one or more (same or different) $C_{1-4}$-alkyl and $C_{2-4}$-alkenyl groups and halogen atoms. Preferably, any $C_{1-6}$-alkyl is methyl, ethyl, isopropyl, n-butyl or hexyl, any $C_{5-7}$-cycloalkyl is cyclopentyl or cyclohexyl, any aryl-$C_{1-4}$-alkyl is benzyl, and, respectively, any aryl is unsubstituted phenyl or naphthyl. Hal is preferably chlorine or bromine. Especially preferred examples of quaternary ammonium salts of formula IIIa are tetramethylammonium chloride, tetraethylammonium chloride, tetraethylammonium bromide and benzyltrimethylammonium chloride, and especially preferred examples of quaternary phosphonium salts of formula IIIb are tetrabutylphosphonium bromide, tetraphenylphosphonium chloride and tetraphenylphosphonium bromide.

The carbon dioxide used in the process in accordance with the invention is gaseous carbon dioxide, which is conveniently introduced into the reaction vessel, suitably a pressure autoclave, which already contains the remaining reaction partners. An increase in the carbon dioxide pressure above normal pressure increases the reaction velocity. Therefore, the process is conveniently carried out under a carbon dioxide pressure which lies above 1 bar (100 kPa), preferably in the range of about 1 bar to about 30 bar (about 100 kPa to about 3000 kPa). When silver acetate is used as the silver salt catalyst, the preferred pressure lies in the range of about 15 bar to about 25 bar (about 1500 kPa) to about 2500 kPa).

Furthermore, the process in accordance with the invention can be carried out in an inert solvent if desired. For this purpose there is generally suitable a polar protic or aprotic solvent, especially an aliphatic hydrocarbon, such as n-hexane; an aliphatic ether, such as tert.butyl methyl ether; an aliphatic ketone, such as 2-methylbutan-3-one; an aliphatic amide, such as dimethylformamide; or an aromatic hydrocarbon, such as toluene. Aliphatic and aromatic hydrocarbons, as well as aliphatic ethers, are preferred solvents. In general, the use of a solvent is indicated when the educt and/or the product is/are solid under the reaction conditions (since the respective melting point(s) is/are too high). Unless necessitated because of insufficient solubility of the educt and/or of the product, the process in accordance with the invention is preferably carried out without the use of a solvent.

With respect to the ratios, there are conveniently used per mol of educt of formula II about 0.05 to about 0.3 mol % of silver salt catalyst and about 0.05 to about 0.3 mol % of onium salt catalyst (quaternary ammonium salt of formula IIIa and/or quaternary phosphonium salt of formula IIIb).

The process in accordance with the invention is conveniently effected in the temperature range of about 25° C. (that is, at room temperature) to about 100° C.

The catalytic performance of the various silver salts differ. It has further been found in connection with the present invention that the performance of the silver salts which have a rather low catalytic activity, such as silver orthophosphate, silver oxide and silver carbonate, can be increased by adding a catalytic enhancer which is an alkali metal or quaternary ammonium or phosphonium salt of a carboxylic acid, with the respective quaternary ammonium or phosphonium ion being especially the aforementioned and defined ion $(R^3)_4N^+$ or $(R^3)_4P^+$, respectively. For this purpose, an about equimolar amount of the carboxylic acid salt with respect to the amount of silver salt is suitably added. Examples of carboxylic acid salts which come into consideration are sodium acetate, potassium monoethyl malonate, disodium maleate as well as tetraethylammonium acetate. The alkali metal and quaternary ammonium and phosphonium acetates are preferred.

A further feature of the present invention comprises carrying out the process in the presence of triphenylphosphine. The addition of triphenylphosphine advantageously accelerates the reaction somewhat. Conveniently, up to about 0.2 mol % of triphenylphosphine can be used per mol of educt of formula II.

In general, the process in accordance with the invention can be performed as a continuous procedure or as a one-pot process (discontinuously).

The working up of the mixture obtained after completion of the reaction in order to isolate the desired 4,4-disubstituted 5-methylene-1,3-dioxolan-2-one of formula I can be effected in a manner known per se. It has been found to be especially practical to obtain the cyclocarbonate from the mixture by fractional distillation. In most cases the catalyst-containing residues can be used for further reaction batches or separated out into the components which can then be reused.

In the case of unstable cyclocarbonates the purification can be effected by chromatography.

The advantage of the subject process over previously known processes for the manufacture of cyclocarbonates is primarily that the inventive silver salts catalyze the respective reaction significantly better than known copper salts. This means that the reaction is catalyzed by much smaller amounts of catalyst, reaction time is significantly shortened, and less drastic reaction conditions are required.

The invention is illustrated by the following Examples:

EXAMPLE 1

Manufacture of 4,4-dimethyl-5-methylene-1,3-dioxolan-2-one 54.68 g (0.65 mol) of 2-methyl-3-butyn-2-ol are placed in a steel autoclave fitted with a manometer, thermometer, safety valve and connection for carbon dioxide gasification. 107 mg (0.41 mmol, 0.063 mol %) of triphenylphosphine, 68 mg (0.41 mmol, 0.063 mol %) of silver acetate as well as 137 mg (0.81 mmol, 0.125 mol %) of tetraethylammonium chloride are added thereto. Then, the autoclave is closed and flushed with carbon dioxide by introducing carbon dioxide up to a pressure of about 20 bar (2000 kPa) with disconnected stirrer and subsequently again releasing pressure; the cycle pressurization and depressurization is carried out three times.

Subsequently, pressurization is carried out to 15 bar (1500 kPa) of carbon dioxide and the reaction mixture is heated to 80° C. within about 20 minutes while stirring. When the temperature has reached 80° C., the internal pressure is increased to about 20 bar (2000 kPa). The mixture is stirred further at 20 bar (2000 kPa) and 80° C. After 3 hours the pressure is reduced to 5 bar (500 kPa) and the temperature is lowered to 40° C. Once the internal temperature has reached 40° C., pressure is carefully released to normal pressure. (A large amount of carbon dioxide dissolves in the product under pressure, so that the pressure must accordingly be reduced very slowly in order to prevent foaming of the reaction mixture.) Since the melting point of the thus-produced cyclocarbonate exceeds 30° C., it need not be cooled to room temperature.

The mixture is then transferred into a distillation apparatus in which it is fractionated by vacuum distillation. The internal temperature is increased initially to 40° C. and at the same time the apparatus is carefully evacuated. The still partially dissolved carbon dioxide thereby bubbles off. After the apparatus has been evacuated to about 10 mbar (1 kPa) the temperature of the oil bath is increased slowly to 100° C. Thereby, the product begins to distil. Head temperature 67°–69° C., pressure 12 mbar (1.2 kPa).

After completion of the distillation there remains behind a dark residue, which is dissolved in methylene chloride and discarded.

In this manner there are obtained 78.59 g (98.66% content) of 4,4-dimethyl-5-methylene-1,3-dioxolan-2-one; the yield is 93.1% based on the methylbutynol used.

EXAMPLE 2
Manufacture of 4-ethyl-4-methyl-5-methylene-1,3-dioxolan-2-one

According to the methodology described in Example 1 and starting from 63.79 g (0.65 mol) of 3-methyl-1-pentyn-3-ol there are obtained 74.54 g (99.99% content) of 4-ethyl-4-methyl-5-methylene-1,3-dioxolan-2-one; the yield is 80.67% based on the methylpentynol used.

EXAMPLE 3
Manufacture of 4-methyl-4-(4-methyl-3-pentenyl)-5-methylene-1,3-dioxolan-2-one According to the methodology described in Example 1, but with a heating period of 8 hours at 20 bar (2000 kPa) and 80° C., and starting from 68.51 g (0.45 mol) of 3,7-dimethyl-oct-1-yn-6-en-3-ol (dehydrolinalool) there are obtained 69.41 g (97.79% content) of 4-methyl-4-(4-methyl-3-pentenyl)-5-methylene-1,3-dioxolan-2-one; the yield is 76.9% based on the dehydrolinalool used.

EXAMPLE 4
Manufacture of 4-methylene-1,3-dioxa-spiro-[4,5]-decan-2-one

According to the methodology described in Example 1, but with a heating period of 5 hours at 20 bar (2000 kPa) and 80° C., and starting from 80.82 g (0.65 mol) of 1-ethynyl-cyclohexanol there are obtained 78.59 g (99.99% content) of 4-methylene-1,3-dioxa-spiro-[4,5]-decan-2-one; the yield is 71.2% based on the ethynylcyclohexanol used.

EXAMPLE 5
Manufacture of 4-methyl-4-(2-methyl-propyl)-5-methylene-1,3-dioxolan-2-one According to the methodology described in Example 1, but with a heating period of 8 hours at 20 bar (2000 kPa) and 80° C., and starting from 70.0 g (0.549 mol) of 3,5-dimethyl-hex-1-yn-3-ol there are obtained 60.15 g (99.7% content) of 4-methyl-4-(2-methyl-propyl)-5-methylene-1,3-dioxolan-2-one; the yield is 62.17% based on the 3,5-dimethyl-hex-1-yn-3-ol used.

EXAMPLE 6
Manufacture of 4-methyl-5-methylene-4-vinyl-1,3-dioxolan-2-one

According to the methodology described in Example 1, but with a heating period of 5 hours at 20 bar (2000 kPa) and 80° C., and starting from 85.45 g (0.800 mol) of 3-methyl-pent-1-en-4-yn-3-ol there are obtained 86.23 g (98.4% content) of 4-methyl-5-methylene-4-vinyl-1,3-dioxolan-2-one; the yield is 75.7% based on the 3-methyl-pent-1-yn-4-en-3-ol used.

EXAMPLE 7
Manufacture of 4,4-diethyl-5-methylene-1,3-dioxolan-2-one

According to the methodology described in Example 1, but using 0.25 mol % triphenylphosphine, 0.25 mol % silver acetate and 0.5 mol % tetraethylammonium chloride and starting from 70.81 g (0.625 mol) of 3-ethyl-1-pentyn-3-ol there are obtained after heating at 20 bar (2000 kPa) and 80° C. for 21 hours, 78.13 g (96.5% content) of 4,4-diethyl-5-methylene-1,3-dioxolan-2-one; the yield is 77.2% based on 3-ethyl-1-pentyn-3-ol used.

EXAMPLE 8
Manufacture of 4-methyl-4-isopropyl-5-methylene-1,3-dioxolan-2-one

According to the methodology described in Example 1, but using 0.25 mol % triphenylphosphine, 0.25 mol % silver acetate and 0.5 mol % tetraethylammonium chloride and starting from 65.0 g (0.572 mol) of 2,3-dimethyl-pent-4-yn-3-ol there are obtained after heating at 20 bar (2000 kPa) and 80° C. for 4 hours, 73.8 g (98.7% content) of 4-methyl-4-isopropyl-5-methylene-1,3-dioxolan-2-one; the yield is 81.5% based on the 2,3-dimethyl-pent-4-yn-3-ol used.

EXAMPLE 9
Manufacture of 4-(4,8-dimethyl-nonyl)-4-methyl-5-methylene-1,3-dioxolan-2-one According to the methodology described in Example 1, but using 0.25 mol % triphenylphosphine, 0.25 mol % silver acetate and 0.5 mol % tetraethylammonium chloride and starting from 50.24 g (0.217 mol) of 3,7,11-trimethyl-dodec-1-yn-3-ol there are obtained after heating at 20 bar (2000 kPa) and 80° C. for 6 hours, 44.36 g (99% content) of 4-(4,8-dimethyl-nonyl)-4-methyl-5-methylene-1,3-dioxolan-2-one; the yield is 75.4% based on the 3,7,11-trimethyl-dodec-1-yn-3-ol used.

EXAMPLE 10
Manufacture of 4-(4,8 dimethyl-nona-1,3,7-trienyl)-4-methyl-5-methylene-1,3-dioxolan-2-one According to the methodology described in Example 1, but using 0.25 mol % triphenylphosphine, 0.25 mol % silver acetate and 0.5 mol % tetraethylammonium chloride and starting from 77.98 g (0.250 mol) of 3,7,11-trimethyl-dodeca-4,6,10-trien-1-yn-3-ol there are obtained after heating at 25 bar (2500 kPa) and 60° C. for 22 hours and purification not by distillation but by column chromatography on silica gel with hexane/diisopropyl ether (17:1) as the eluent 41.4 g (93% content) of 4-(4,8-dimethyl-nona-1,3,7-trienyl)-4-methyl-5-methylene-1,3-dioxolan-2-one; the yield is 58.3% based on the 3,7,11-trimethyl-dodeca-4,6,10-trien-1-yn-3-ol used.

EXAMPLE 11

Manufacture of various 4,4-disubstituted 5-methylene-1,3-dioxolan-2-ones using silver or copper acetate as the silver/copper salt catalyst: a comparison The "ethynyl alcohols" 2-methyl-3-butyn-2-ol, 3-methyl-1-pentyn-3-ol, 2-phenyl-3-butyn-2-ol and 1-ethynyl-1-cyclohexanol are reacted in succession with carbon dioxide using silver or copper acetate as the catalyst according to the following general procedure:

650 mmol of ethynyl alcohol are placed in a steel autoclave fitted with a manometer, thermometer, safety valve and connection for carbon dioxide gasification. 0.41 mmol (0.063 mol %) of triphenylphosphine, 0.41 mmol (0.063 mol %) of silver or copper acetate and 0.82 mmol (0.125 mol %) of tetraethylammonium chloride are added thereto. The autoclave is closed and flushed with carbon dioxide. Subsequently, pressurization is carried out to 15 bar (1500 kPa) of carbon dioxide and the reaction mixture is heated to 80° C. within about 20 minutes while stirring. Once the reaction temperature has reached 80° C,. the internal pressure is increased to 20 bar (2000 kPa). The mixture is stirred further at 20 bar (2000 kPa) and 80° C. and a sample is removed every hour and analyzed by gas chromatography. After completion of the reaction the pressure is released to 5 bar (500 kPa) and the temperature is lowered to 40° C. When the internal temperature has reached 40° C., pressure is released carefully to normal pressure.

The reaction mixture is transferred into a distillation apparatus in which it is fractionated by vacuum distillation. The internal temperature is increased initially to 40° C., during which the apparatus is carefully evacuated. The still partially dissolved carbon dioxide thereby bubbles out. After the apparatus has been evacuated to about 10 mbar (1 kPa) the temperature of the oil bath is increased slowly until the product begins to distil.

After completion of the distillation there remains behind a dark residue, which is dissolved in methylene chloride and discarded.

The results of the analyses are compiled in Table 1 hereinafter:

TABLE 1

Carboxylation of ethynyl alcohols under catalysis by silver or copper acetate [$AgOCOCH_3$ or $Cu(OCOCH_3)_2$]

| Educt (ethynyl alcohol) | Catalyst | Percentage content (according to gas chromatography, area percent) of cyclocarbonate in the reaction mixture after hours: | | | | | |
|---|---|---|---|---|---|---|---|
| | | 1 | 2 | 3 | 4 | 5 | 6 |
| 2-Methyl-3-butyn-2-ol | $AgOCOCH_3$ | 92.6 | 98.3 | 99.5 | | | |
| | $Cu(OCOCH_3)_2$ | 36.8 | 66.9 | 83.0 | 89.4 | 93.1 | 94.7 |
| 3-Methyl-1-pentyn-3-ol | $AgOCOCH_3$ | 74.9 | 95.1 | 100 | | | |
| | $Cu(OCOCH_3)_2$ | 17.0 | 35.4 | 51.2 | 65.8 | | |
| 2-Phenyl-3-butyn-2-ol | $AgOCOCH_3$ | 46.4 | 60.6 | 64.0 | 66.6 | 67.7 | 67.7 |
| | $Cu(OCOCH_3)_2$ | 0.8 | 1.8 | 3.3 | 4.6 | 7.1 | 8.8 |
| 1-Ethynyl-1-cyclohexanol | $AgOCOCH_3$ | 54.2 | 77.4 | 92.0 | 98.4 | 99.6 | |
| | $Cu(OCOCH_3)_2$ | 5.0 | 8.3 | 15.6 | 31.9 | 32.8 | 41.5 |

EXAMPLE 12

Manufacture of 4,4-dimethyl-5-methylene-1,3-dioxolan-2-one under various reaction conditions 2-Methyl-3-butyn-2-ol was reacted with carbon dioxide ($CO_2$) under catalysis by silver acetate or copper acetate according to the procedure of Example 11. The process was carried out once under standard conditions [at 80° C. and 20 bar (2000 kPa) $CO_2$ pressure], once under normal pressure [at 80° C. and 1 bar (100 kPa) $CO_2$ pressure] and once at room temperature [at 25° C. and 20 bar (2000 kPa) $CO_2$ pressure]. The results are compiled in Table 2 hereinafter:

TABLE 2

Carboxylation at various reaction temperature and pressures

| Conditions (Temperature/pressure) | Catalyst | Percentage content (according to gas chromatography, area percent) of cyclocarbonate in the reaction mixture after hours: | | | | | |
|---|---|---|---|---|---|---|---|
| | | 1 | 2 | 3 | 4 | 5 | 6 |
| 80° C./20 bar (2000 kPa) | $AgOCOCH_3$ | 92.6 | 98.3 | 99.5 | | | |
| | $Cu(OCOCH_3)_2$ | 36.8 | 66.9 | 83.0 | 89.4 | 93.1 | 94.7 |
| 80° C./1 bar (100 kPa)* | $AgOCOCH_3$ | 6.9 | 13.0 | 23.3 | 33.9 | 44.2 | 56.7 |
| | $Cu(OCOCH_3)_2$ | 3.3 | 8.3 | 11.6 | 19.7 | 25.0 | 33.4 |

TABLE 2-continued

Carboxylation at various reaction temperature and pressures

| Conditions (Temperature/pressure) | Catalyst | Percentage content (according to gas chromatography, area percent) of cyclocarbonate in the reaction mixture after hours: | | | | | |
|---|---|---|---|---|---|---|---|
| | | 1 | 2 | 3 | 4 | 5 | 6 |
| 25° C./20 bar (2000 kPa)* | AgOCOCH$_3$ | 7.7 | 11.8 | 15.6 | 19.6 | 23.0 | 26.7 |
| | Cu(OCOCH$_3$)$_2$ | 0.8 | 2.4 | 4.0 | 6.1 | 8.8 | 10.0 |

EXAMPLE 13

Manufacture of 4,4-dimethyl-5-methylene-1,3-dioxolan-2-one under catalysis by various silver salt catalysts 2-Methyl-3-butyn-2-ol was reacted with carbon dioxide under catalysis by various silver salt catalysts according to the procedure of Example 11. The results are compiled in Table 3 hereinafter:

TABLE 3

Carboxylation under catalysis by various silver salt catalysts

| Catalyst | Percentage content (according to gas chromatography, area percent) of cyclocarbonate in the reaction mixture after hours: | | |
|---|---|---|---|
| | 1 | 2 | 3 |
| Silver sulphate | 89.2 | 98.3 | 99.7 |
| Silver acetate | 87.7 | 98.7 | 100 |
| Silver orthophosphate | 37.4 | 46.3 | 51.3 |
| Silver oxide | 23.8 | 36.2 | 47.4 |
| Silver carbonate | 18.0 | 24.8 | 35.9 |

EXAMPLE 14

Manufacture of 4,4-dimethyl-5-methylene-1,3-dioxolan-2-one under catalysis by silver nitrate or trifluoroacetate with added carboxylic acid alkali metal salt 2-Methyl-3-butyn-2-ol was reacted with carbon dioxide under catalysis by silver nitrate or trifluoroacetate and added carboxylic acid alkali metal salt according to the procedure of Example 11. The carboxylic acid alkali metal salt was used in each case in an equimolar amount based on the amount of silver salt, and the remaining catalyst components were used in two-fold amounts. The results are compiled in Table 4 hereinafter:

TABLE 4

Carboxylation under catalysis by silver nitrate or trifluoroacetate and various carboxylic acid alkali metal salt

| Added carboxylic acid alkali metal salt/silver salt | Percentage content (according to gas chromatography, area percent) of cyclocarbonate in the reaction mixture after hours: | | | |
|---|---|---|---|---|
| | 1 | 2 | 3 | 4 |
| Sodium acetate/silver nitrate | 84.6 | 98.8 | 99.4 | |
| Potassium monoethyl malonate/silver trifluoroacetate | 72.4 | 89.0 | 93.8 | 95.6 |
| Disodium maleate/silver trifluoroacetate | 15.1 | 27.0 | 44.0 | 54.1 |

EXAMPLE 15

Manufacture of 4,4-dimethyl-5-methylene-1,3-dioxolan-2-one using various solvents 2-Methyl-3-butyn-2-ol was reacted with carbon dioxide according to the procedure of Example 11, but with the additional use of a solvent. 1.5 ml of solvent were added per gram of methylbutynol. The results are compiled Table 5 hereinafter:

TABLE 5

Carboxylation using various solvents

| Solvent | Percentage content (according to gas chromatography, area percent) of cyclocarbonate in the reaction mixture after hours: | | | | | |
|---|---|---|---|---|---|---|
| | 1 | 2 | 3 | 4 | 6 | 8 |
| n-Hexane | 22.2 | 69.3 | 74.1 | 81.1 | 88.8 | 93.7 |
| tert.Butyl methyl ether | 27.4 | 56.2 | 76.2 | 81.4 | 89.5 | 91.9 |
| Toluene | 53.5 | 87.8 | 94.9 | 98.7 | 99.4 | 100 |

Upon reading the present specification, various alternative embodiments will become obvious to the skilled artisan. These variations are to be considered within the scope and spirit of the invention which is only to be limited by the claims that follow and their equivalents.

What is claimed is:

1. A process for manufacturing 4,4-disubstituted 5-methylene-1,3-dioxolan-2-ones of the formula:

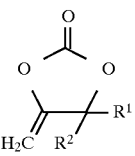

I wherein $R^1$ and $R^2$ each independently is a saturated aliphatic group, an olefinically-unsaturated aliphatic group or an aromatic group, or $R^1$ and $R^2$ together form tetramethylene or pentamethylene, which comprises reacting a corresponding 3,3-disubstituted prop-1-yn-3-ol of the formula:

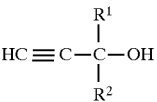

II with carbon dioxide in the presence of a first catalyst selected from the group consisting of quaternary ammonium salts and quaternary phosphonium salts, and a second catalyst which is a silver salt.

2. The process according to claim 1, wherein the second catalyst is selected from the group consisting of silver acetate, silver sulphate, silver orthophosphate, silver oxide, and silver carbonate.

3. The process according to claim 2, wherein the second catalyst is silver acetate or silver sulphate.

4. The process according to claim 1, wherein the first catalyst is a quaternary ammonium salt.

5. The process according to claim 4, wherein the quaternary ammonium salt is selected from the group consisting of tetramethylammonium chloride, tetraethylammonium chloride, tetraethylammonium bromide, and benzyltrimethylammonium chloride.

6. The process of claim 1, wherein the first catalyst is a quaternary phosphonium salt.

7. The process according to claim 6, wherein the quaternary phosphonium salt is selected from the group consisting of tetrabutylphosphonium bromide, tetraphenylphosphonium chloride, and tetraphenylphosphonium bromide.

8. The process according to claim 1, wherein the reacting is in the presence of a catalytic enhancer selected from the group consisting of an alkali metal salt of a carboxylic acid, a quaternary ammonium salt of a carboxylic acid, and a quaternary phosphonium salt of a carboxylic acid.

9. The process of claim 8, wherein the catalytic enhancer is selected from the group consisting of sodium acetate, potassium monoethyl malonate, disodium maleate, and tetraethylammonium acetate.

10. The process according claim 1, wherein the reacting is in the presence of triphenylphosphine.

11. The process according to claim 1, wherein the reacting is in the presence of (i) a catalytic enhancer selected from the group consisting of an alkali metal salt of a carboxylic acid, a quaternary ammonium salt of a carboxylic acid, and a quaternary phosphonium salt of a carboxylic acid, and (ii) triphenylphosphine.

12. The process according to claim 10, wherein the reacting is in the presence of about 0.05 to about 0.3 mol % of the first catalyst, about 0.05 to about 0.3 mol % of the second catalyst, and up to about 0.2 mol % triphenylphosphine, per mol of educt of formula II, and the reacting is also in the presence of about an equimolar amount of the catalytic enhancer with respect to the amount of second catalyst.

13. The process according to claim 1, wherein the reacting is effected under a carbon dioxide pressure of from about 1 bar to about 30 bar.

14. The process according to claim 1, wherein the reacting is effected in a temperature range of from about 25° C. to about 100° C.

15. The process according to claim 2, wherein the first catalyst is a quaternary ammonium salt.

16. The process according to claim 15, wherein the quaternary ammonium salt is selected from the group consisting of tetramethylammonium chloride, tetraethylammonium chloride, tetraethylammonium bromide, and benzyltrimethylammonium chloride.

17. The process of claim 2, wherein the first catalyst is a quaternary phosphonium salt.

18. The process according to claim 17, wherein the quaternary phosphonium salt is selected from the group consisting of tetrabutylphosphonium bromide, tetraphenylphosphonium chloride, and tetraphenylphosphonium bromide.

19. The process according claim 2, wherein the reacting is in the presence of triphenylphosphine.

20. The process according to claim 2, wherein the reacting is in the presence of (i) a catalytic enhancer selected from the group consisting of an alkali metal salt of a carboxylic acid, a quaternary ammonium salt of a carboxylic acid, and a quaternary phosphonium salt of a carboxylic acid, and (ii) triphenylphosphine.

21. The process according to claim 3, wherein the first catalyst is a quaternary ammonium salt.

22. The process according to claim 21, wherein the quaternary ammonium salt is selected from the group consisting of tetramethylammonium chloride, tetraethylammonium chloride, tetraethylammonium bromide, and benzyltrimethylammonium chloride.

23. The process of claim 3, wherein the first catalyst is a quaternary phosphonium salt.

24. The process according to claim 23, wherein the quaternary phosphonium salt is selected from the group consisting of tetrabutylphosphonium bromide, tetraphenylphosphonium chloride, and tetraphenylphosphonium bromide.

25. The process according claim 3, wherein the reacting is in the presence of triphenylphosphine.

* * * * *